United States Patent [19]

Moring

[11] Patent Number: 5,110,431
[45] Date of Patent: May 5, 1992

[54] ON-CAPILLARY GAP JUNCTION FOR FLUORESCENCE DETECTION IN CAPILLARY ELECTROPHORESIS

[75] Inventor: Stephen E. Moring, Sunnyvale, Calif.

[73] Assignee: Applied Biosystems, Inc., Foster City, Calif.

[21] Appl. No.: 486,893

[22] Filed: Feb. 28, 1990

[51] Int. Cl.⁵ .............................. G01N 27/26
[52] U.S. Cl. .................. 204/180.1; 204/183.3; 204/299 R
[58] Field of Search ............ 204/180.1, 183.3, 299 R

[56] References Cited

U.S. PATENT DOCUMENTS

| | | | |
|---|---|---|---|
| 4,676,897 | 6/1987 | Kuze et al. | 204/183.3 |
| 4,936,974 | 6/1990 | Rose et al. | 204/299 R |
| 4,994,165 | 2/1991 | Lee et al. | 204/299 R |

FOREIGN PATENT DOCUMENTS 356160  2/1990  European Pat. Off. .

OTHER PUBLICATIONS

Pentoney et al., "On-Line Connector for Microcolumns...", Anal. Chem. 60(1988) pp. 2625-2629.
Caprioli et al., "Coupling Capillary Zone Electrophoresis...", Journal of Chromatography, 480(1989) pp. 247-257.
Donald J. Rose, Jr., et al, Post-Capillary Fluorescence Detection In Capillary..., Journal of Chromatography, 447 (1988), 117-131.
Sciex Product Note on Capillary Zone Electrophoresis.
Edgar D. Lee, et al, "Liquid Junction Coupling for Capillary Zone...", Biomedical & Environmental Mass Spectrometry, v. 0, 1989.

Primary Examiner—John Niebling
Assistant Examiner—David G. Ryser
Attorney, Agent, or Firm—John A. Frazzini

[57] ABSTRACT

A junction reactor that aligns a pair of capillaries substantially collinearly, end-to-end that allows a small gap to be produced between these two ends. An applied voltage difference between the other ends of these two capillaries produces in the gap electric field lines that extend across the gap. Empirical evidence shows that the gap introduces only a small reduction in resolution of an electrophoretic or electrochromatographic separation. The gap enables sample liquid to be coupled between capillaries of different internal diameters and enables on-capillary reactions such as attaching a fluorescent tag to a sample components.

27 Claims, 11 Drawing Sheets

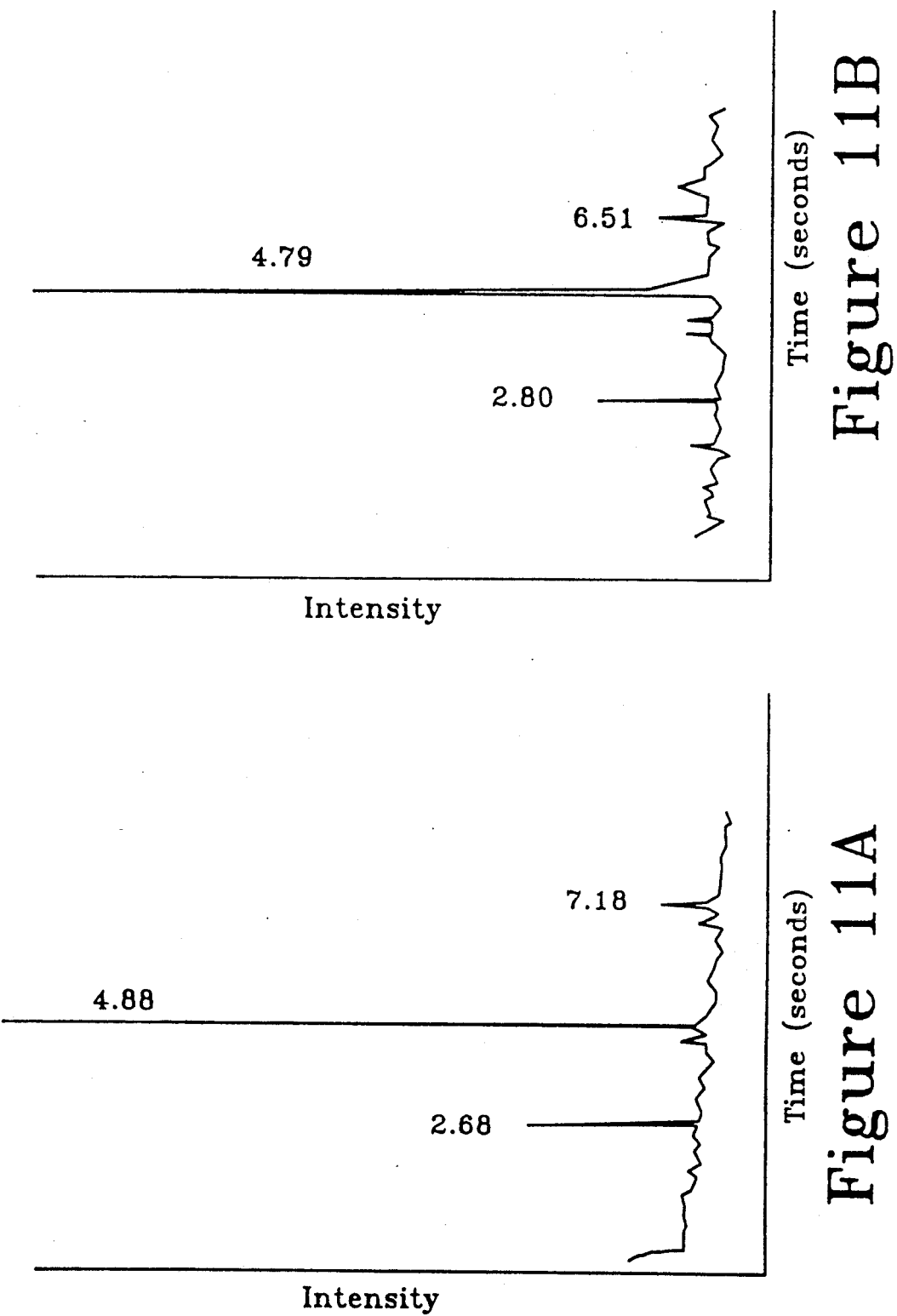

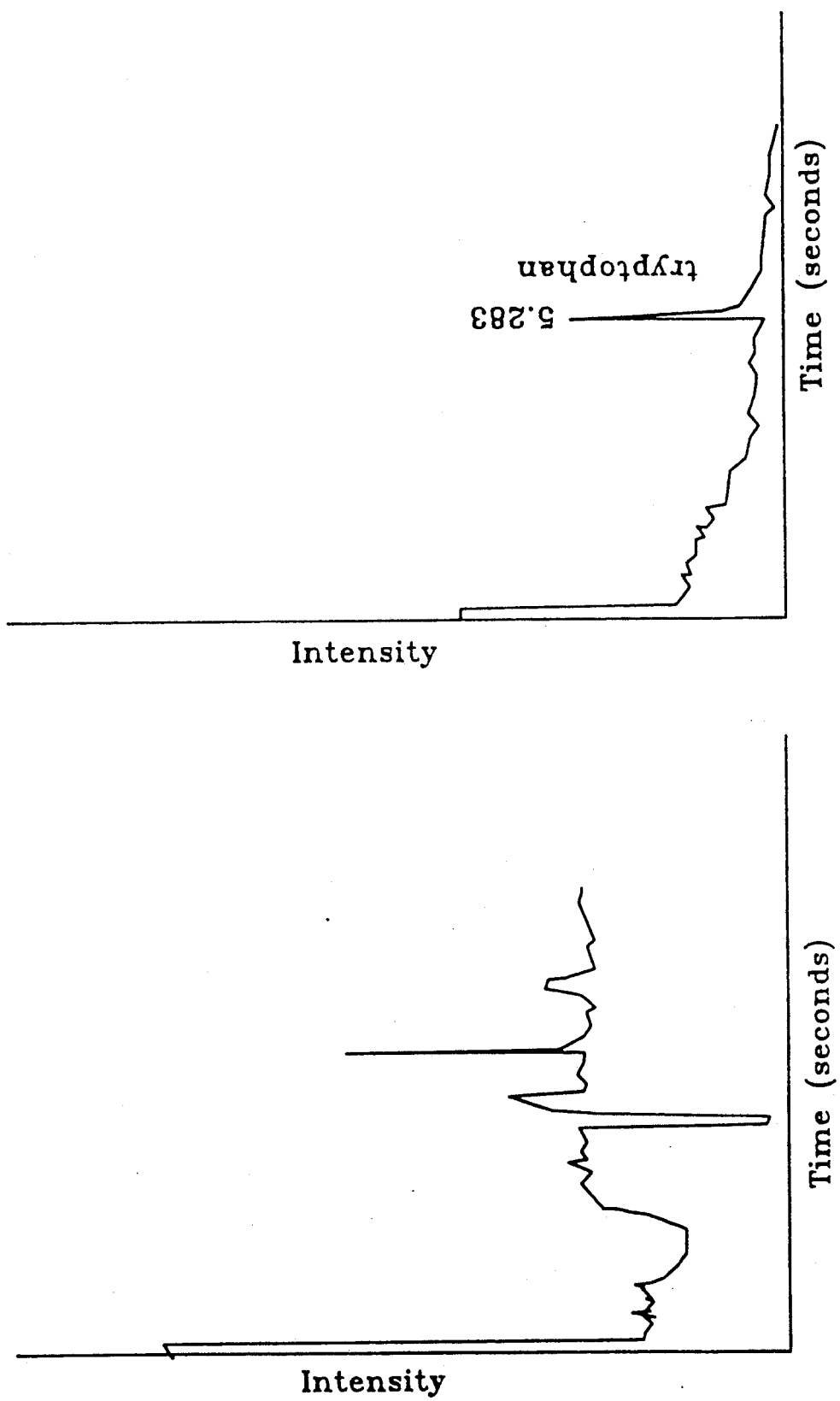

ON-CAPILLARY GAP JUNCTION FOR FLUORESCENCE DETECTION IN CAPILLARY ELECTROPHORESIS

In the figures, the first digit of a reference numeral indicates the first figure in which is presented the element indicated by that reference numeral.

BACKGROUND OF THE INVENTION

This invention relates generally to capillary electrophoresis and more particularly to the use of a capillary having a gap across which electric field lines serve to contain sample flow and minimize solute zone broadening.

In FIG. 1 is illustrated an apparatus for electrophoretic separations and electro-chromatography. A first buffer solution 11 is contained in a container such as beaker 13 and a second buffer solution 12 is contained in a second container such as beaker 14. Inlet end 19 of a capillary 15 is immersed in beaker 13 and exit end 110 of capillary 15 is immersed in beaker 14. A voltage source 16 having a high voltage electrode 17 immersed in the first buffer solution and a ground electrode 18 immersed in the second buffer solution produces between these solutions a voltage difference on the order of 5-30 kV. This voltage difference produces a current through capillary 15 on the order 1-150 $\mu$A. Capillary 15 has an inside diameter on the order of 2-200 $\mu$m and a length that is typically in the range from 5 cm to 2 meters. Although the typical range of capillary diameters is 2-200 $\mu$m, other diameters can also be used.

In FIG. 2 is illustrated in greater detail a small section of capillary 15. The interior cavity 20 of capillary 15 is filled with a conductive liquid referred to as the "support electrolyte". The inside surface of the wall 21 of capillary 15 consists of silane and silicic acid groups 22 (which in this embodiment are positive, but for other choices of support electrolyte and wall 21 can be negative), thereby leaving an excess of positively charged ions 23 in the body 24 of the support electrolyte near the wall. Voltage source 16 produces an electric field $\bar{E}$ that drives positively charged liquid body 24 toward the cathode of voltage source 16. In addition, positively charged particles are driven toward the cathode and negatively charged particles, such as particle 25, are driven toward the anode of voltage source 16. Sample is loaded into capillary 15 by applying a vacuum to the exit end 110 of the capillary or by immersing the inlet end of the capillary into a vial containing the sample and briefly turning on the electric field to draw some of the sample into the capillary. The inlet end 19 of the capillary is then reinserted into beaker 13 and the electric field is turned on to draw sample ions from beaker 13 through capillary 15.

Many biological molecules are amphoteric so that the pH of the support electrolyte can be selected to control the sign of charge on selected sample components. Because of this ability to control the charge of sample components, sample component separation can be achieved by control of the charge of the sample components. However, because biological molecules have a greater variation in size and shape than in charge, for separation of biological molecules, it is advantageous to fill interior cavity 20 of capillary 15 with a gel having a pore size selected to separate selected components of the sample as the primary separation mode.

Detection of the sample components can be achieved by several different mechanisms, including UV absorption, fluorescence, refractive index, conductivity or electrochemical detection. This is typically achieved either by making the measurement in the electrolye while it is within capillary 15 or as it emerges from the exit end 110 of capillary 15. Detection of the fluid within the capillary is generally favored because the detection cell 111 is a part of the capillary and therefore is simple to implement and avoids solute zone broadening that typically occurs as the sample emerges from exit end 110.

For UV absorption measurements, a UV beam is directed through capillary tube 15 to a photodetector to record absorption spectra of the sample. Capillary 15 typically has a polyamide protective coating that is burned off in the region of detection cell 111 so that it does not interfere with transmission of light through the capillary. In general, a capillary is just a tube typically having an inside diameter of 1-700 microns and an outside diameter of 0.16 centimeters.

To maximize the signal to noise ratio of a measurement, it is important to pass substantially all of the UV light through the electrolyte. This requires that the UV light beam be centered onto capillary 15 and that the beam diameter be smaller than the internal bore of capillary 15. Because of the small diameter of the capillary precision alignment of the UV beam is required. Because the capillary wall is curved and much thicker than the internal bore of the capillary, small misalignment of the beam can bend the beam, thereby accentuating this misalignment. This can result in a significant fraction of the beam passing outside of the stream of electrolyte.

For fluorescence detection, a fluorescent "tag" is attached to the sample molecules. The tag can be attached before or after electrophoretic separation of the components. However, because the tag can change the charge state of its attachment site thereby affecting the electrophoretic separation, it is preferred that it be attached after separation so that it does not interfere with the separation process. This is particularly important for samples that have multiple tag attachment sites. Also, some tags, such as o-phthaldialdehyde (OPA) that is used to tag amine groups, decompose at a rate that is amino acid-dependent. Therefore, it is advantageous to tag the sample just ahead of entry into detection cell 111.

A post-capillary reactor suitable for introducing the fluorescent tag immediately ahead of the fluorescence detector is presented in the article by Donald J. Rose and James W. Jorgenson entitled Post-Capillary Fluorescence Detector In Capillary Zone Electrophoresis Using o-Phthaldialdehyde, Journal of Chromatography, 447 (1988) 117-131. This reactor is illustrated in FIG. 3 and a test system incorporating this reactor is illustrated in FIG. 4. This reactor 30 is in the form of a tee 41 having a set of three ferrules 31-33 that respectively receive exit end 110 of capillary 15, an inlet end 34 of a reaction capillary 35 and an end 36 of a reagent capillary 37.

For high resolution, it is important that sample solute zones be as narrow as possible. To avoid broadening these zones, the outer diameter $D_e$ of electrophoresis capillary 15 is smaller than the inner diameter $d_r$ of reaction capillary 35 so that capillary 15 can be inserted a short distance into capillary 35. Because of the small capillary diameters, this insertion step requires the use of a microscope. A tag reagent reservoir 42 is at a height $\Delta h$ above reservoirs 13 and 14 so that hydrostatic pressure forces tag reagent into end 34 of reaction capillary 35.

In an alternate embodiment, exit end 110 of electrophoretic capillary 15 is dipped into an etchant to reduce its outer diameter. This is done to reduce zone broadening caused by turbulent flow of reagent past the blunt exit end of electrophoretic capillary 15. The need to use a microscope to insert this end into reaction capillary 35, the time needed to carefully etch exit end 110 and the fragility of this etched end significantly increase the manufacture and assembly time of this reactor.

In the article Stephen L. Pentoney, Jr., Xiaohua Huang, Dean S. Burgi and Richard N. Zare, On-Line Connector for Microcolumns: Application to the on-Column O-Phthaldialdehyde Derivatization of Amino Acids Separated by Capillary Zone Electrophoresis, Anal. Chem., 2625-2629, vol. 60 (1988), a microcolumn connector is presented in which a laser is used to produce a pair of aligned holes through opposite sides of a 75 $\mu$m diameter capillary. A pair of smaller diameter capillaries are inserted into these holes to produce an inlet and an outlet path for flow from a capillary zone electrophoresis (CZE) apparatus. Chemicals flow in the 75 $\mu$m diameter capillaries to derivatize the CZE flow in the smaller diameter capillaries, for example to attach a fluorescent tag to the chemicals separated by CZE.

As is illustrated by these references, it is desirable to have a mechanism for exposing a CZE stream to other chemicals for derivatization without degrading the resolution of the component (peak) zones in the CZE stream. Unfortunately, both of these connectors are relatively time expensive and time consuming to fabricate because of the need to align and assemble fragile connector components under a microscope.

SUMMARY OF THE INVENTION

In accordance with the illustrated preferred embodiment, a junction reactor is presented that is particularly useful for mixing of reagent buffers on-capillary with electrophoretic and micellar chromatographic separations. This reactor provides a functional union of two capillaries that are separated by a buffer-filled gap. This reactor enables reagent mixing via the gap without significant dispersion or degradation of the electrophoretic and micellar separations. It also enables the serial use of two different functional type of capillaries, such as open tubular coated capillaries and gel filled capillaries, thereby enabling the separation capabilities of both of these types of processes to be applied sequentially to a given sample.

In this reactor, an exit end of a first capillary is aligned end to end and substantially colinearly with an inlet end of a second capillary where these two ends are separated by a small gap. The portions of these two capillaries within this junction are immersed in a buffer that can provide reagents that are mixed with the electrophoretic or micellar separations.

The flow rates of fluid in the two capillaries can be controlled to draw a controlled amount of fluid into the second capillary. Flow rate control can be achieved by control of a number of parameters, such as the inside diameters of the capillaries, the pressure drop across each capillary, the coatings on the inner surfaces of the capillaries, the inclusion of a packing material in one or both of the capillaries and the potential drop and length of each capillary. In contrast to this, in capillary zone electrophoresis, the flow $F_{eo}$ is determined primarily by the applied voltage, the buffer ionic strength, the buffer viscosity, and the inner surface area of the capillary wall.

Reagents can be selected to attach a fluorescent tag to the sample components to enable fluorescent detection of the components. The on-capillary nature of this reaction is advantageous for several reasons. The sample components can be tagged immediately ahead of the fluorescent detector so that there is insufficient time between attaching the tag and making the fluorescent measurements for the tag to decay before reaching the detector. Also, the presence of the tag can significantly affect the electrophoretic or micellar separation process. Therefore, it is advantageous to minimize the distance that the tagged sample travels before it reaches the detector.

For electrophoretic separations, a voltage difference $V_1$ is applied between the buffer at the inlet end of the first of these two capillaries and the buffer at the exit end of the second of these two capillaries. This voltage difference produces within both capillaries an electrophoretic movement of ions that can be used to electrophoretically separate components of a sample that is supplied to the input end of the first capillary.

The buffer-filled gap can also be utilized as part of an improved mechanism for exposing sample liquid with a light beam in absorbance and fluorescence detection. In the case of absorbance detection, a first optical fiber directs light through this gap to a second optical fiber that directs this light to a photodetector. In fluorescence detection, passage of the light through the buffer-filled gap avoids the scattering of light by surfaces of a sample-carrying capillary as is common in the prior art. By eliminating this source of scatter, this mechanism will reduce the background noise, thereby significantly increasing the signal-to-noise ratio for such measurements.

Empirical results show that the gap does not significantly broaden sample component zones. It is speculated that the electric field lines from the exit end of the first capillary to the entrance end of the second capillary constrain the radial flow of sample within the gap and substantially eliminate broadening of the solute zones as they cross the gap.

These and other objectives and advantages of the present invention will become clear from the detailed description given below in which a preferred embodiment is described in relation to the drawings. The detailed description is presented to illustrate the present invention, but is not intended to limit it.

DESCRIPTION OF THE FIGURES

FIG. 11A illustrates fluorescence data when the capillaries have a 50 micron gap and a 25 micron offset.

FIG. 11B illustrates the fluorescence data when the capillaries have a gap of 400 microns.

FIGS. 14A and 14B illustrate the use of reactor 50 for separation of tryptophan and histidine.

DESCRIPTION OF THE PREFERRED EMBODIMENT

Figure 1:
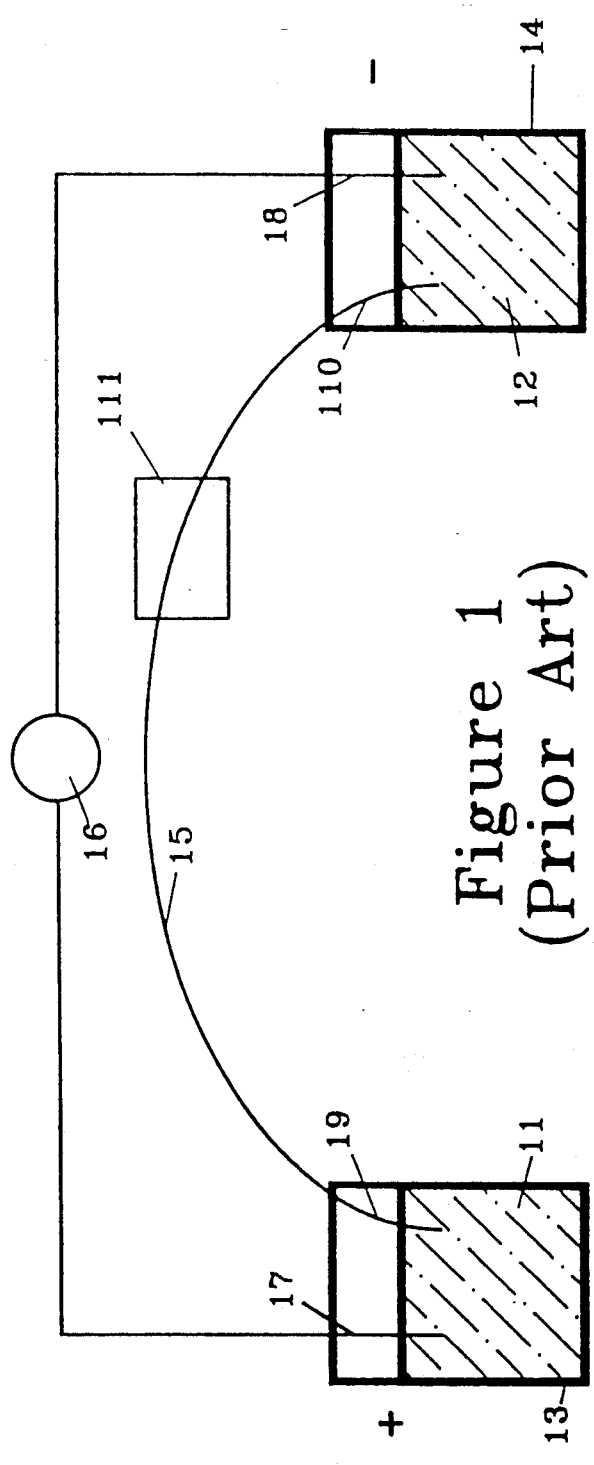
FIG. 1 illustrates a conventional apparatus for electrophoretic separation chromatography.
Figure 2:
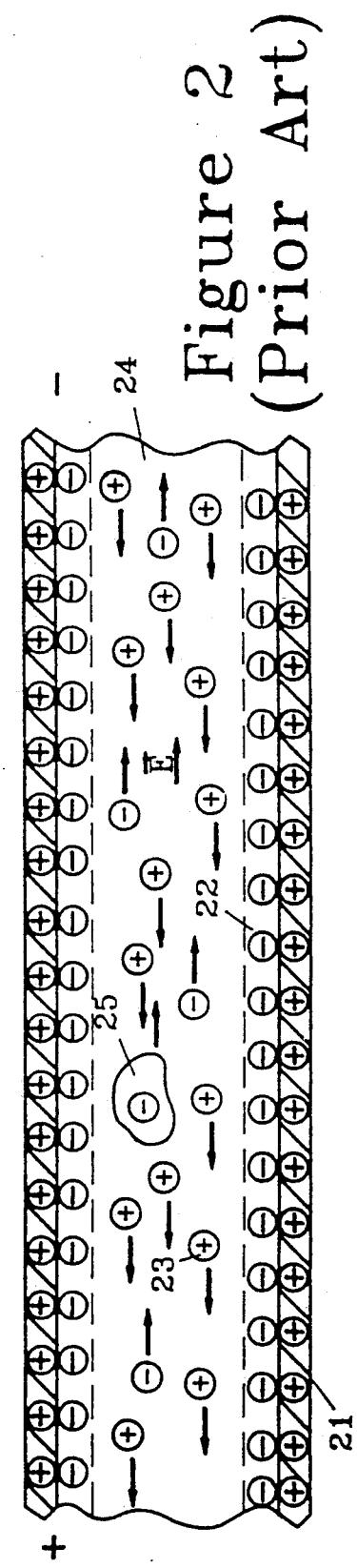
FIG. 2 illustrates in greater detail a cross-section of the capillary in the apparatus of FIG. 1.
Figure 3:
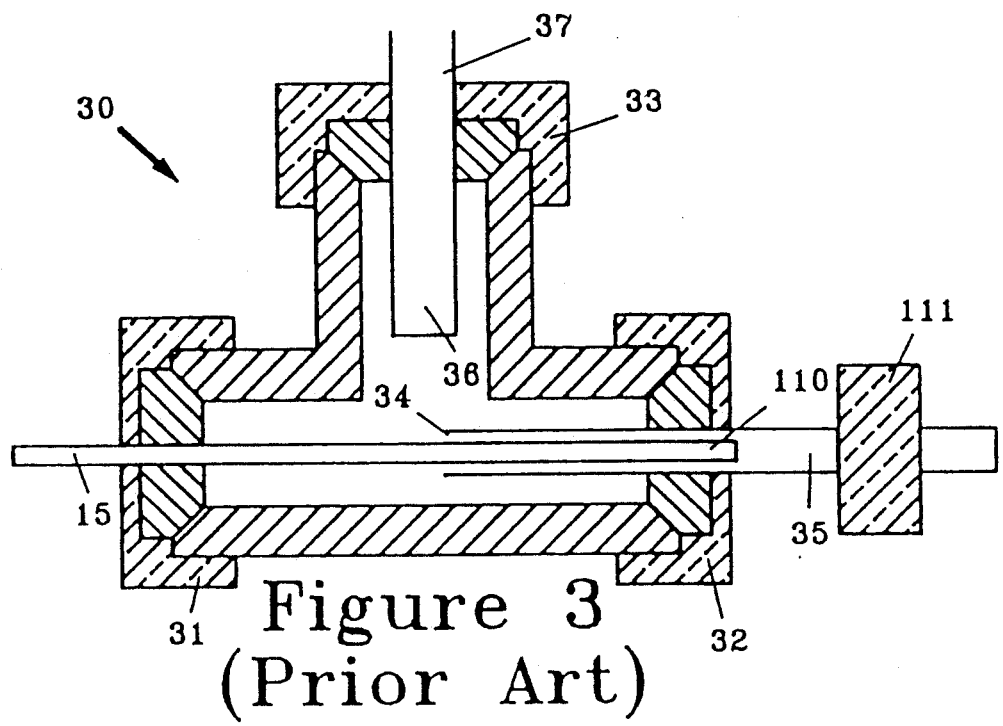
FIG. 3 illustrates a prior art T-shaped reactor in which a first capillary extends into the second capillary.
Figure 4:
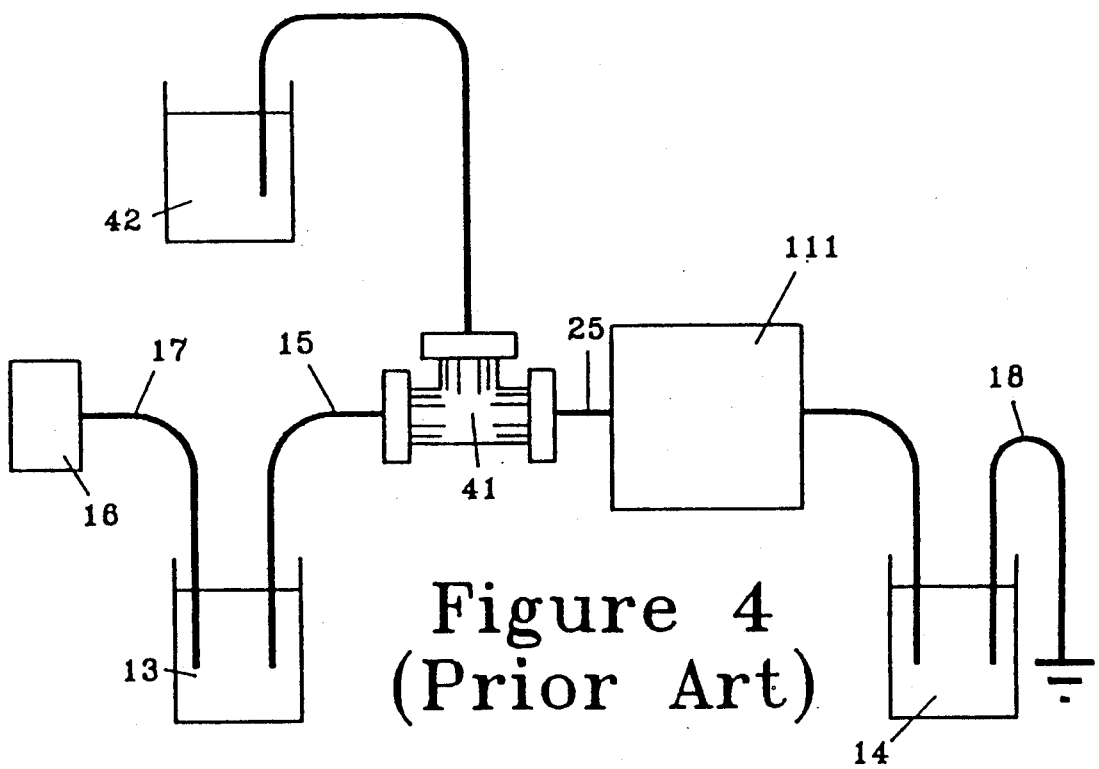
FIG. 4 illustrates the use of the reactor of FIG. 3 in an electrophoretic separation apparatus.
Figure 5A:
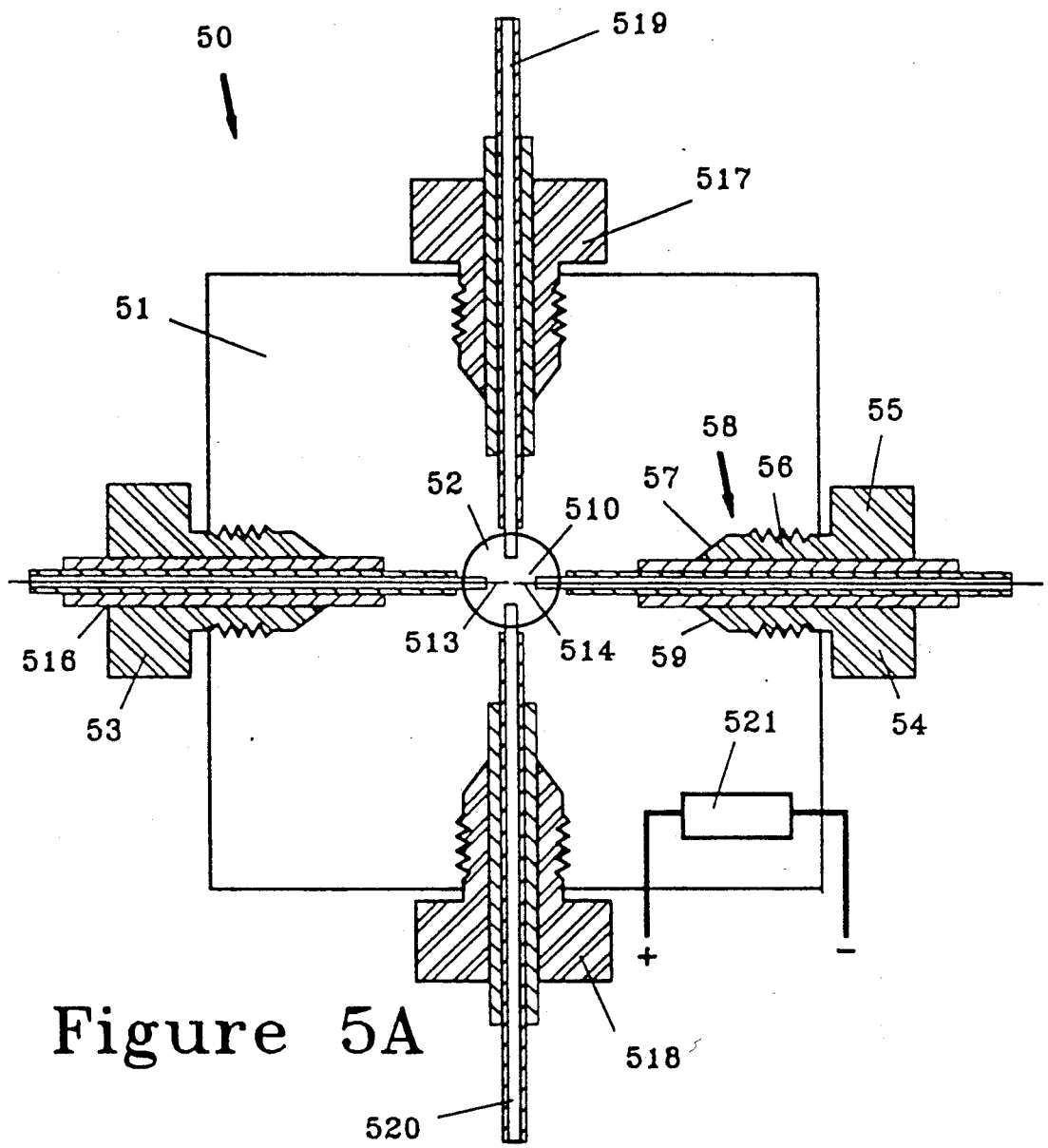
FIG. 5A illustrates an on-capillary gap junction reactor that is particularly useful in capillary electrophoresis and micellar electrokinetic chromatography.
Figure 5B:
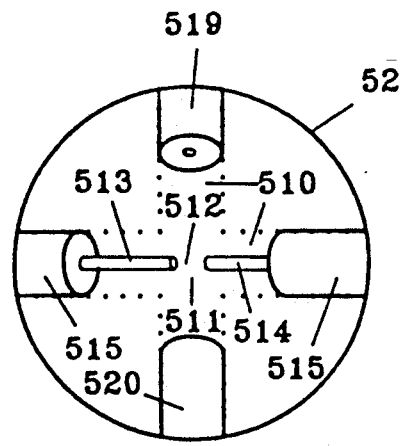
FIG. 5B is an enlarged view of the gap junction reactor illustrating in greater detail the portion of this reactor adjacent to the gap junction.

FIG. 5 illustrates an on-capillary gap junction reactor 50 that is particularly useful in capillary electrophoresis and micellar electrokinetic chromatography. This reactor consists of a 2.5 cm wide by 2.5 cm high by 1 cm thick body 51 of a transparent, nonconductive material such as plexiglass or polymethyl pentene, a lens 52 and a pair of plastic fittings 53 and 54. Polymethyl pentene is a particularly useful choice of material for the body because it is clear and chemically inert. This enables a user to see inside this reactor and avoids reaction of the body with the reagents that pass through this reactor.

Fittings 53 and 54 are commercially available from Optimize Technology and include a head 55, a threaded section 56, and a tapered end 57 that functions as a ferrule when this fitting is tightened into a hole 58 in body 51. Hole 58 is threaded to receive the threads 56 of a fitting and has a tapered end 59 to compress end 57 of a fitting so that it functions as a ferrule. Holes 58 and a set of 0.16 cm diameter channels 510 can be machined into body 51. Lens 52 is glued onto the side of body 51 to magnify an intersection 511 of these channels to enable adjustment of a small gap 512 between a pair of capillaries 513 and 514 inserted through fittings 53 and 54, respectively. Gap 512 has a length typically in the range 1-400 microns and preferably in the range 20-50 microns.

Each of capillaries 513 and 514 has an outside diameter of 375 microns and an inner diameter that can be chosen in a range typically from 2-200 microns. Each of these capillaries is slipped into a teflon tube 515 of outside diameter 0.16 cm and inside diameter 275 microns so that each teflon tube fits snugly around its capillary. To enable the capillary to be pushed through the narrower teflon tube, a flaring tool, such as a needle, is pushed into a first end of the teflon tube to flare it slightly. The teflon is resilient enough that the larger diameter capillary is easily slipped through this tube to extend about 1-2 mm past the other end of the teflon tube.

The teflon jacketed section of each capillary is then pushed through a 0.16 cm bore 516 through its associated fitting and the fitting is lightly tightened into body 51 to produce a snug, water-tight fit of tapered end 57 against that capillary. When these fittings are screwed into holes 58, the teflon jacketed capillaries extend into channels 510. The small amount of friction of the teflon sleeves enables capillaries 513 and 514 to be pushed farther through fittings 53 and 54, respectively to adjust gap 512 to a user selected value, typically in the range 1-100 microns. During the process of adjusting the gap, a magnifying glass is held in front of lens 52 to produce a sufficiently magnified image of the intersection 511 of the channels that the desired gap can be selected.

Figure 6:
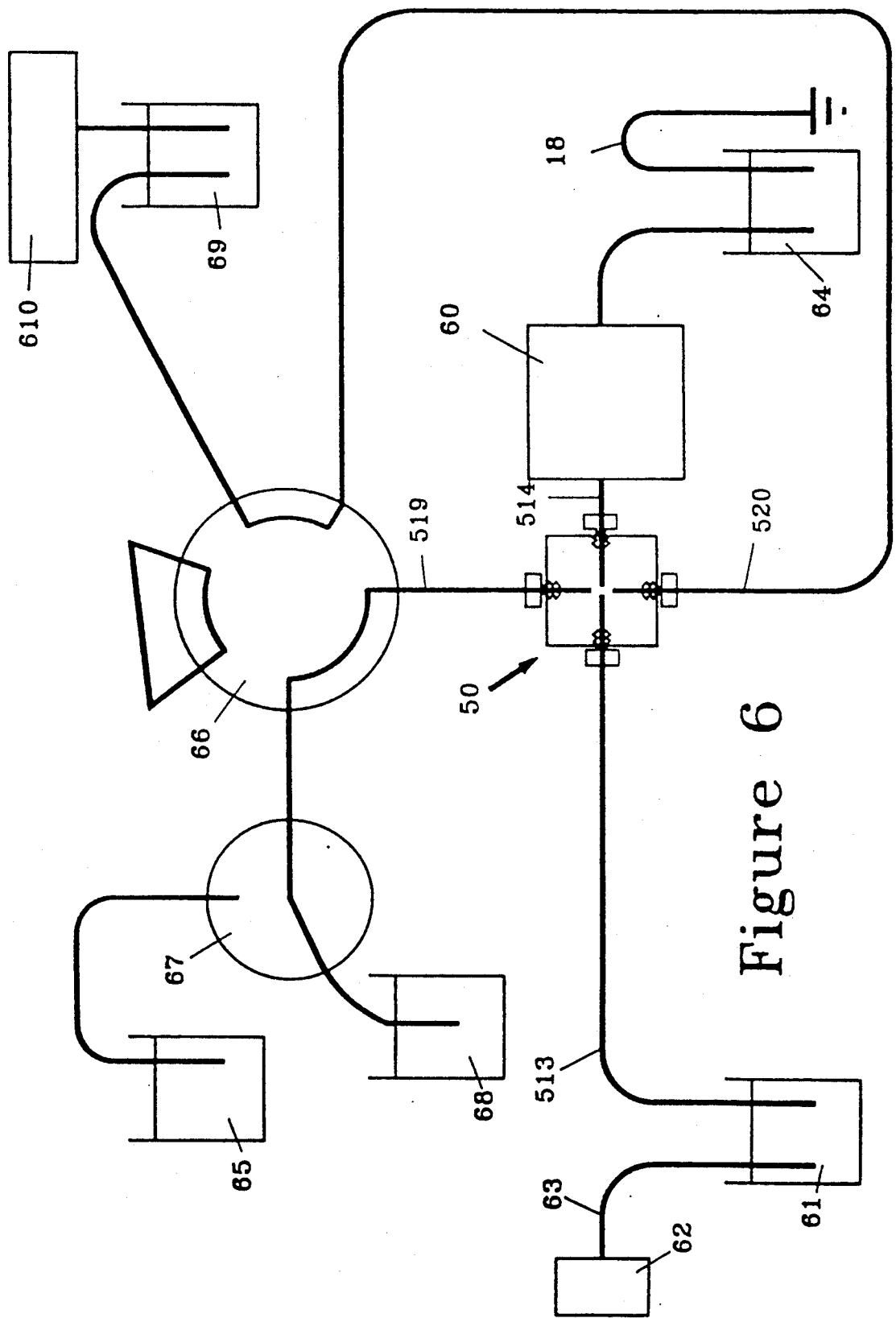
FIG. 6 illustrates a capillary zone electrophoresis apparatus utilizing the reactor of FIG. 5.

A reactor having only fittings 53 and 54 can be used to couple the test liquid travelling through capillary 513 into capillary 514. However, to enable air bubbles to be removed from intersection 511 and to enable flow of the reagent liquid as it passes across gap 512 and through capillary 514, additional fittings and associated holes are included in reactor 50. In the embodiment of FIG. 5, two additional holes 58 and fittings 517 and 518 are included to enable an additional pair of capillaries or 0.16 cm diameter plastic tubing 519 and 520 to be coupled to the reactor. "Capillaries" are just tubes having an inside diameter typically in the range 1-700 microns and outside diameter 0.16 cm. The utility of these additional capillaries is illustrated in FIG. 6 in which is presented an electrophoretic apparatus that utilizes an on-capillary gap junction for fluorescent detection.

An inlet end of capillary 513 is immersed briefly in a sample solution to draw in a small amount of sample solution and then this inlet end is immersed in an anodic buffer in a buffer reservoir 61. A positive voltage from a high voltage supply 62 is applied to the anodic buffer by an electrode 63 that is also immersed in the anodic buffer. An exit end of capillary 514 is immersed in a cathodic buffer in a grounded buffer reservoir 64. This applied voltage produces electrophoretic flow of charged solute molecules in capillaries and 514 to separate the different components of the sample solution. Capillary 514 passes through a fluorescence detector 111 for fluorescent detection of the electrophoretically separated components of the sample liquid.

To enable fluorescent detection of these components, it is necessary to attach a fluorescent tag to the components. Because this tag typically has a short decay time and can interfere with electrophoretic separation, it is advantageous to apply this tag immediately ahead of the fluorescent detector. This is achieved by the inclusion of an additional capillary 519 that is connected to a reagent reservoir 65 that contains a reagent that can react with the sample solution to attach the fluorescent tag. The fluorescent detector is a short distance (on the order of 5-8 centimeters) from reactor 50 so that only a small amount of fluorescent decay occurs before the tagged sample passes through the fluorescence detector.

Additional capillaries, such as capillary 520, and a valve 66 are connected to reactor 50 to provide additional flexibility for this electrophoretic apparatus. For example, a valve 67 can be activated to connect capillary 519 to an additional buffer reservoir 68 to apply additional reagents to the sample or additional buffer solution. Valve 66 is also connected to a waste reservoir to draw waste liquid from reactor 50. A negative head pressure can be applied to the liquid in reservoir 69 by a vacuum pump 610 or by locating reservoir 68 lower than reactor 50. Thus, reactor 50 enables on-capillary application of buffers and reagents to the sample liquid to facilitate the electrophoretic separation and detection process.

A heater element 521, connected to a remote power source (not shown) is utilized to elevate the temperature of the junction, typically by 10-30 degrees, to speed up reactions. Many reactions are very temperature dependent so that even a few degrees change can significantly affect reaction rate. This is particularly advantageous for the reaction to attach a fluorescent tag because the fluorescence detector is located only a short distance from intersection 511 so that there will be minimal decay in the fluorescence before the tagged sample reaches the detector.

Figure 7:
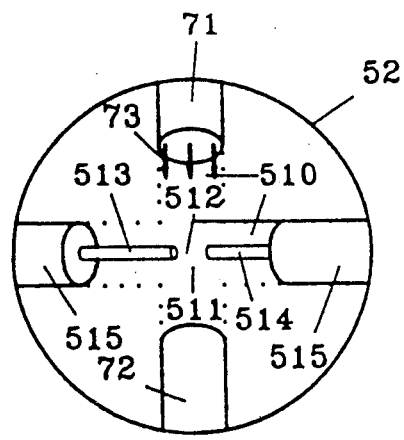
FIG. 7 illustrates the use of this reactor for optical detection through the gap between the capillaries.

Reactor 50 can also be utilized to perform spectrophotometric measurements on the sample solution. For absorbance measurements, this can be achieved by inserting through fittings 517 and 518 a pair of optical fibers 71 and 72 (as is illustrated in FIG. 7) in place of capillaries 519 and 520. Opitcal fiber 71 has an inlet end connected to an optical source to supply an optical beam 73 through gap 512 to fiber 72 which transmits this light on to a photodetector. This structure is advantageous in that light scatter is reduced compared to other optical systems, such as fluorescent detector 60, that pass the optical beam through the curved sides of a capillary. For fluorescence measurements, an optical beam is imaged through lens 52 onto gap 512 and again exhibits reduced light scatter compared to systems that image the light through the side of a capillary. This is particularly important for fluorescence measurements because of the much reduced intensity of the fluorescent light compared to the intensity of the optical beam. The contribution of scattered light to the fluorescent emission from solute molecules (the primary signal) reduces the sensitivity of the overall fluorescence measurement.

Figure 8:
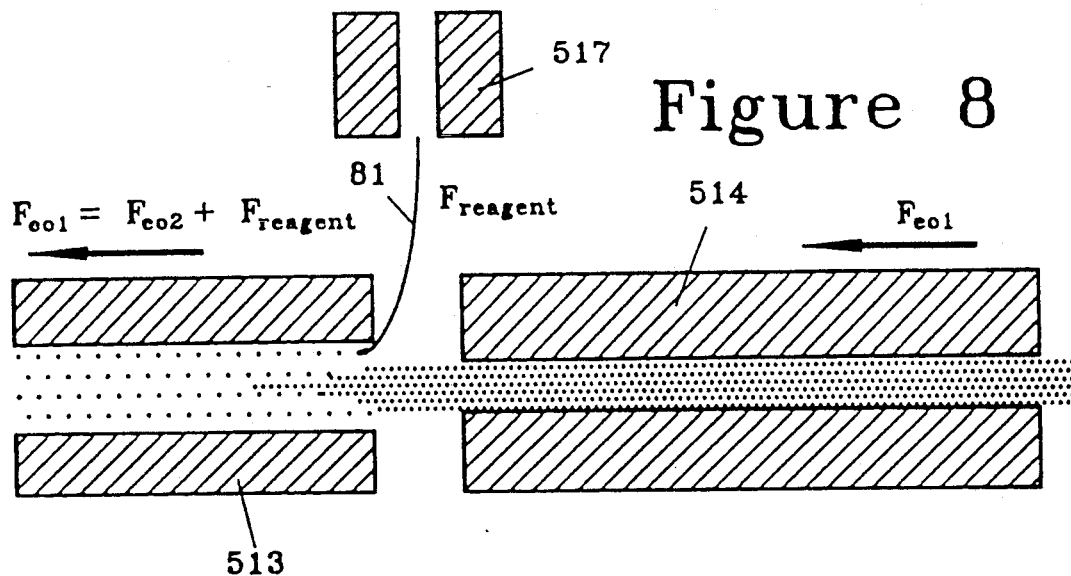
FIG. 8 illustrates the entrainment of fluid bath when the first capillary has a lower electroosmotic flow rate $F_{eo1}$ than the electroosmotic flow rate $F_{eo2}$ in the second capillary.

FIG. 8 illustrates that apparatus parameters can be selected so that the electroosmotic flux $F_{eo1}$ in capillary 513 is less than the electroosmotic flux $F_{eo2}$ in capillary 514. Therefore, in addition to the liquid from capillary 513, buffer or reagent from tube 517 is drawn into capillary 514 as is indicated by flux arrow 81 ($F_{reagent}$). This situation can arise from a number of parameter choices, including: (1) capillaries 513 and 514 are the same except that capillary 514 has a larger internal diameter than that of capillary 513 so that the increased surface area of the inside of capillary 514 produces an increased electroosmotic flow $F_{eo2}$ than that ($F_{eo1}$) that occurs in capillary 513; (2) capillary 513 is packed with a denser packing than capillary 514; or (3) the fluid in capillary 517 elevates the pressure in intersection 511 above what it would be without fluid injection from capillary 517.

Figure 9:
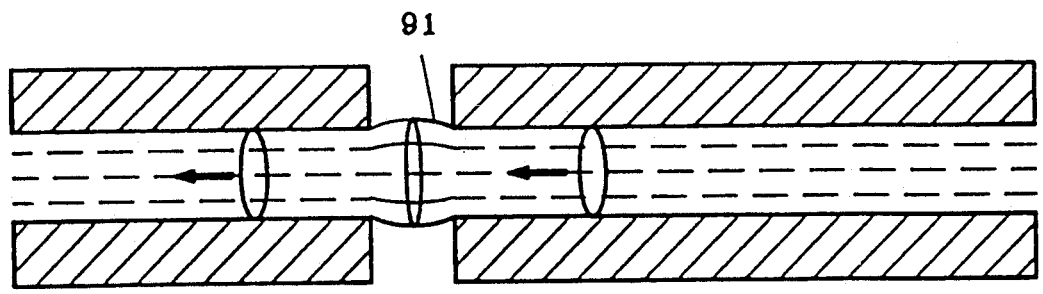
FIG. 9 illustrates electric field and fluid flow lines across the gap in the reactor of FIG. 5.

It is important that reactor 50 does not significantly degrade the resolution of the electrophoretic separation. Experimental results have confirmed that this is indeed the case. It is speculated that the electric field lines 91 (shown in FIG 9) extending from the exit end of capillary 513 to the inlet end of capillary 514 push the sample component ions exiting capillary 513 across gap 512 into capillary 514.

Figure 10B:
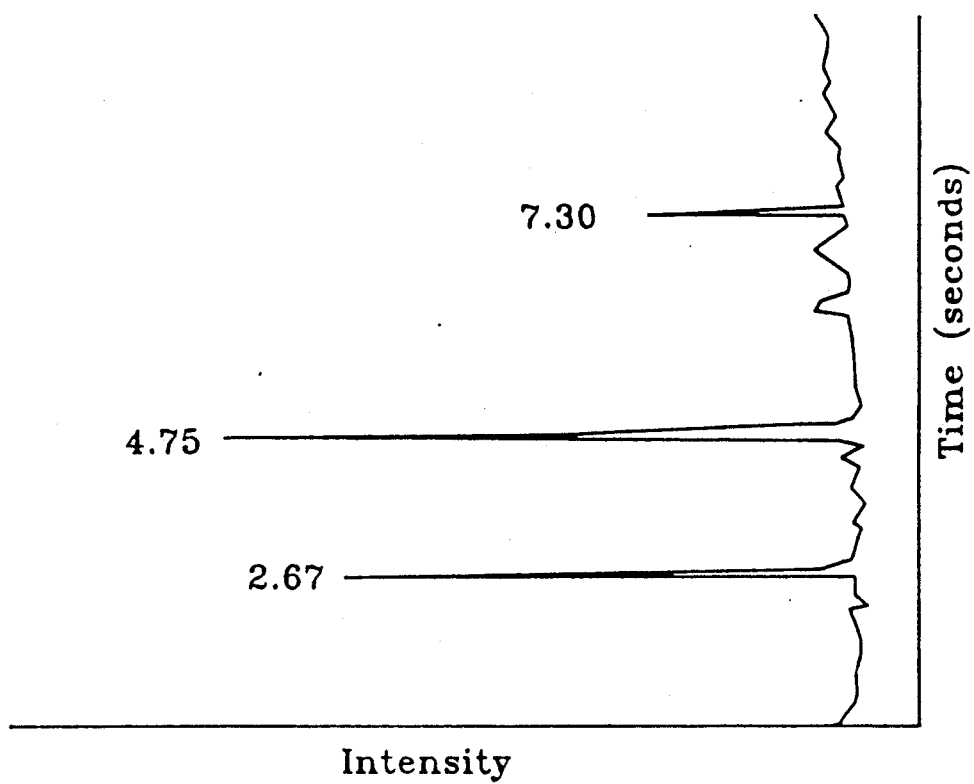
FIG. 10B presents the electrophoretic data for the case of the same capillary after it was carefully broken and then coupled in reactor 50 with an intentional lateral offset of 20 microns.
Figure 10A:
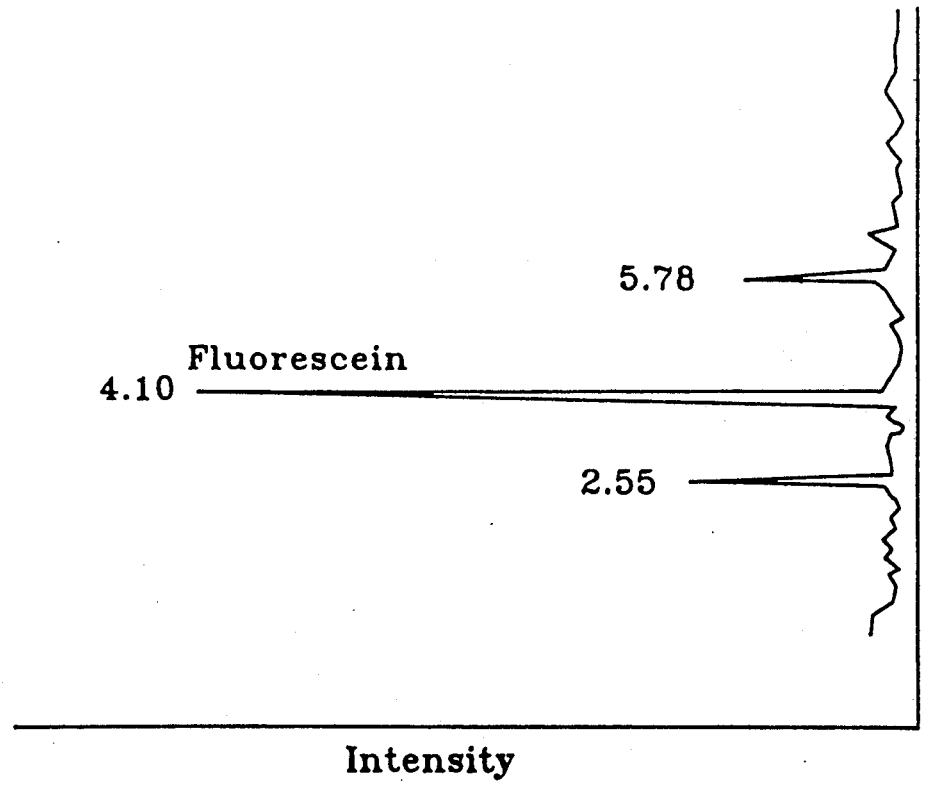
FIG. 10A presents the electrophoretic data for the case of a single electrophoretic 50 micron internal diameter capillary.

FIGS. 10A, 10B, 11A and 11B illustrate the sample peak zone broadening produced by the introduction of a gap into the electrophoretic flow path. These figures illustrate that the peaks are not significantly degraded even when an intentional lateral offset is introduced between the capillaries at intersection 511. FIG. 10A presents the electrophoretic data for the case of a single electrophoretic 100 micron internal diameter capillary and FIG. 10B presents the electrophoretic data for the case of the same capillary after it was carefully broken and then coupled in reactor 50 with a 125 micron gap and a lateral offset of 50 microns. FIG. 11A presents the electrophoretic data for the case of a single electrophoretic 50 micron internal diameter capillary and FIG. 11B presents the electrophoretic data for the case of the same capillary after it was carefully broken and the coupled in reactor 50 with an intentional lateral offset of 20 microns. Although there is a notable effect on the baseline signal, the three primary peaks remain very distinct and the primary peak is broadened only by about a factor of 4.

Figure 12B:
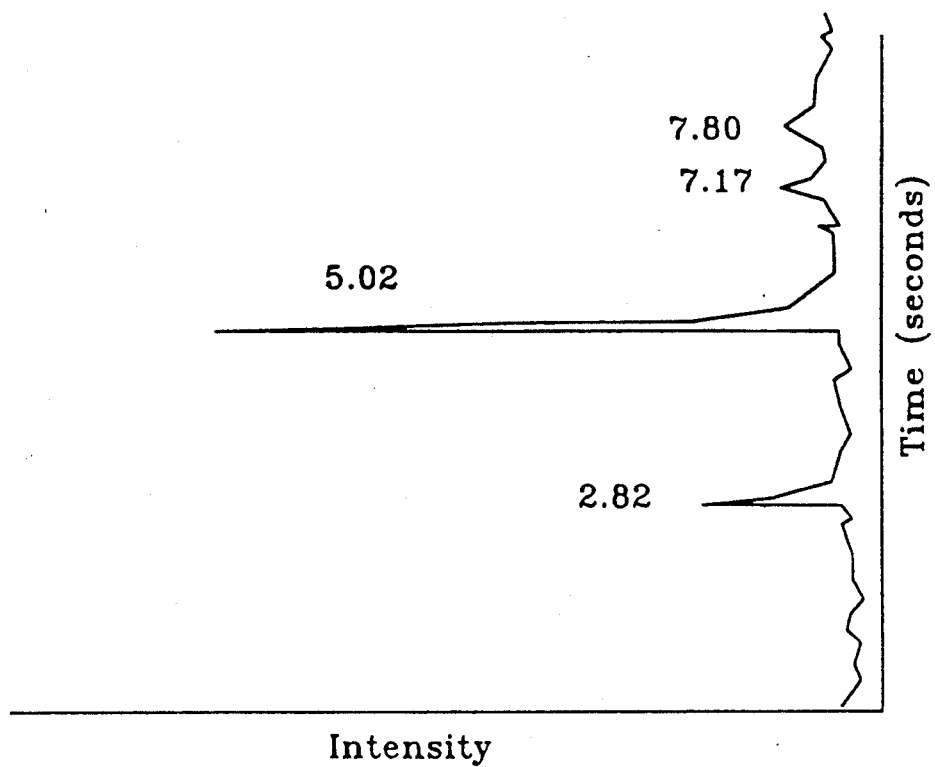
In FIG. 12B, the gap was increased to 400 microns and the resulting spectrum exhibits about a factor of $\frac{1}{2}$ decrease in amplitude and a factor of 2 increase in peak half-width.
Figure 12A:
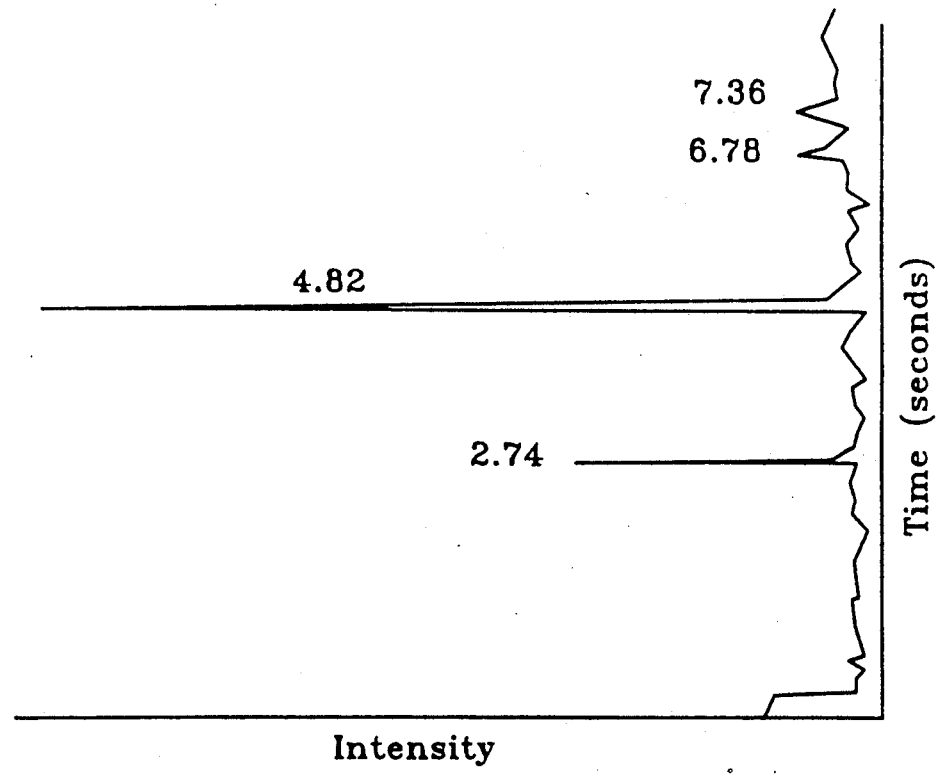
In FIG. 12A, the capillaries had a 50 micron gap and a 25 micron offset.

FIGS. 12A and 12B illustrate the effect of gap size when a 50 micron inside diameter first capillary has its exit end coupled in reactor 50 to the inlet end of a second capillary of 100 micron inside diameter. Because of the difference in internal diameters, some of the buffer within intersection 511 is drawn into the second capillary along with the stream of sample liquid from the first capillary. In FIG. 12A, the capillaries has a 50 micron gap and a 25 micron offset. In FIG. 12B, the gap was increased to 400 microns and the resulting peak exhibits about a factor of ½ decrease in amplitude and a factor of 2 increase in peak half-width.

Figure 13C:
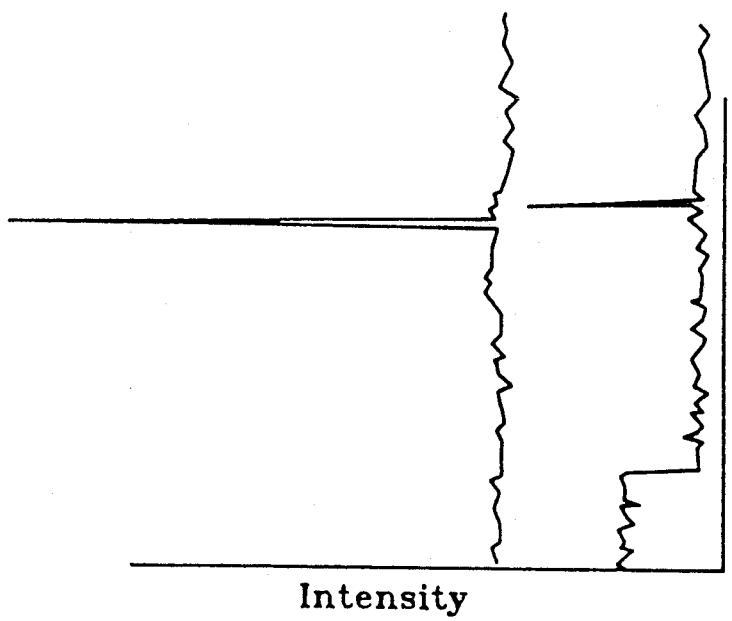
FIGS. 13A-13C illustrate the effect of the height of buffer reservoir 68 relative to buffer reservoirs 61 and 64.
Figure 13B:
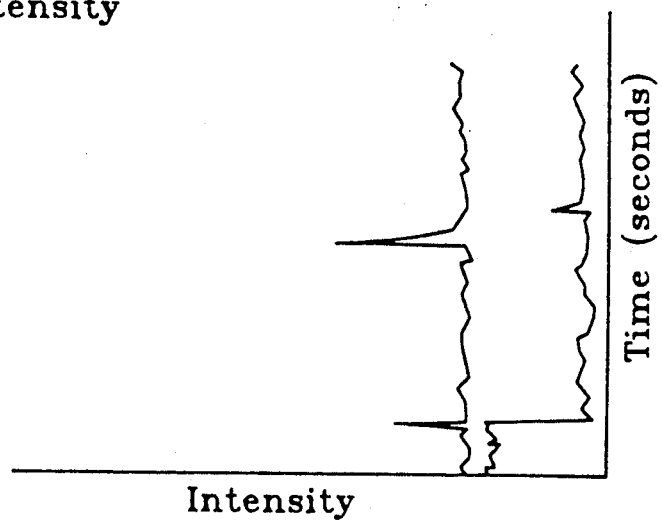
Figure 13A:
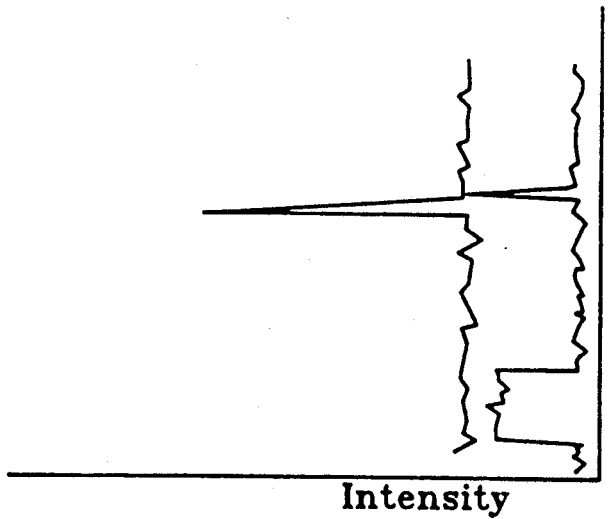

FIGS. 13A and 13B illustrate the effect of the height of buffer reservoir 68 compared to buffer reservoirs 61 and 64. In FIG. 13A, these three buffer reservoirs were at the same height. In FIG. 13B, reservoir 68 was 5 cm higher than reservoirs 61 and 64. The added pressure within reactor 50 results in a reduced flow rate of sample through capillary 514 and an increased dilution of the sample as it passes through the junction. This produces the significantly reduced peak heights in FIG. 13B compared to FIG. 13A. In these figures, the top trace is for a fluorescence detector and the bottom trace is for a UV absorption detector. FIG. 13C shows the results when reservoir 68 was 2 cm below the other two reservoirs.

FIGS. 14A and 14B illustrate the use of reactor 50 for ortho pthaladehyde (OPA) post-column derivatization of tryptophan and histidine that have been separated electrophoretically. These figures present UV absorbance data for these samples. In FIG. 14A, the UV light wavelength was 200 nm and in FIG. 14B, the UV light wavelength was 230 nm. The tryptophan and histidine peaks are indicated in both figures.

Figures 15A, 15B:
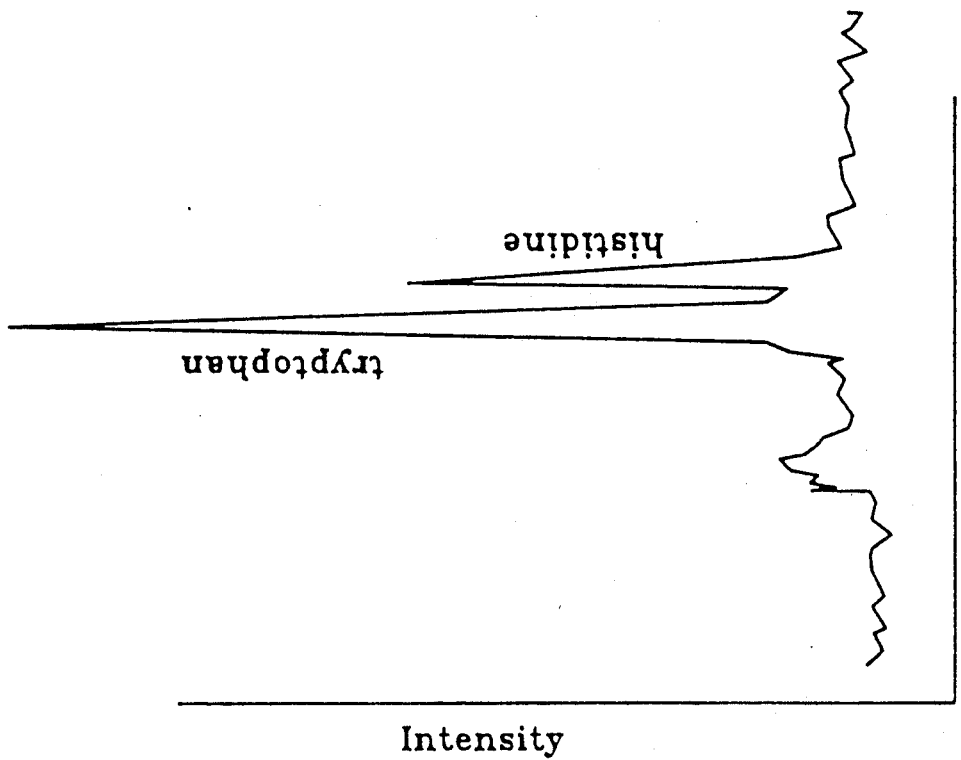
FIGS. 15A and 15B illustrate the change in fluorescent response caused by a 10 Centigrade degree increase in temperature during post column reaction of ortho phthaldehyde with tryptophan and histidine.

FIGS. 15A and 15B illustrate the effect of even a 10 Centigrade degree increase in temperature on the OPA derizatization reaction rate and the concomitant increase in the fluorescence. These figures show significantly stronger fluorescence peaks when the temperature of reactor is held at 40° C. (as in FIG. 13B) than at 30° C. (as in FIG. 13A).

I claim:

1. A method of coupling sample liquid from an exit end of a first capillary into an inlet end of a second capillary, said method comprising the steps of:
   (a) inserting an exit end of said first capillary into a first end of a first channel extending through a gap junction reactor and attaching this capillary to said gap junction reactor utilizing a first fitting;
   (b) inserting the inlet end of said second capillary into a second end of said first channel and attaching this capillary to said gap junction reactor utilizing a second fitting, said first and second fittings each being located such that these fibers are aligned substantially collinearly at the exit end of the first capillary and the inlet end of the second capillary, each of these capillaries being inserted into the reactor to a depth such that an exit end of the first capillary is separated from the inlet end of the second capillary by said gap and these capillaries are nonoverlapping;
   (c) producing a flow of sample liquid through the first capillary, across the gap into the second capillary; and
   (d) producing a nonzero voltage difference between liquid in an exit end of the first capillary and liquid in an inlet end of the second capillary to produce electric field lines that cross from the exit end of the first capillary to the inlet end of the second capillary, whereby sample component zone broadening during passage across the gap is less than if this voltage difference were zero.

2. A method as in claim 1 further comprising the step of:
   (e) controlling the temperature of said reactor, thereby adjusting reaction rates within this reactor.

3. A method as in claim 1 wherein said first and second capillaries have different internal diameters.

4. A method as in claim 1 wherein the exit end of the first capillary and the inlet end of the second capillary are separated by a distance on the order of an inside diameter of one of these two capillaries.

5. A method as in claim 1 wherein, during the step of aligning an exit end of the first capillary end to end with an inlet end of the second capillary,
   (f) viewing the region, containing the gap, through an optical imaging device that magnifies this region, thereby enabling increased accuracy in selecting a desired distance between these two ends.

6. A method as in claim 1 wherein said voltage across the gap is produced by producing a voltage difference between liquid at an inlet end of the first capillary and liquid at an exit end of the second capillary.

7. A method as in claim 1 further comprising the step of:
   (g) imaging a beam of light through said gap.

8. A method as in claim 7 further comprising the step of:
   (h1) utilizing a first optical fiber to collect light travelling from said gap.

9. A method as in claim 8 further comprising before step (g1) the step of:
   (g0) inserting an inlet end of said first optical fiber into a second channel that intersects the first channel; and
   (g0') utilizing a third fitting to attach this optical fiber to said gap junction reactor such that this first inlet end of this optical fiber is positioned and oriented to receive light from said gap.

10. A method as in claim 9 wherein said step of imaging a beam of light through said gap comprises transmitting this beam from an exit end of a second optical fiber that is attached to said junction gap reactor by a fourth fitting;
    wherein said inlet end of the first optical fiber is aligned substantially collinearly with said beam so that this beam passes through the gap to this first optical fiber, whereby this method is particularly suitable for absorbance measurements.

11. A method as in claim 9 wherein said inlet end of the first optical fiber is oriented such that it receives substantially no light directly from said beam of light, whereby this method is particularly suitable for fluorescence detection.

12. A method as in claim 11 wherein step (g) comprises the step of imaging light through a sidewall of the reactor along a direction approximately perpendicular to a plane containing the first channel and the second channel.

13. A method as in claim 7 wherein said light is imaged through said gap without significantly illuminating the first or second capillaries, whereby scatter from such capillaries is substantially reduced.

14. A gap junction reactor for coupling a first capillary and a second capillary such that an exit end of the first capillary is substantially collinear with an inlet end of the second capillary, said junction reactor comprising:
    a body having a first channel therethrough between a first fitting and a second fitting, each of which is attached to said body;
    said first capillary, which is to transport a sample liquid to said second capillary, being inserted through the first fitting and clamped by the first fitting in a first position in which its exit end extends into a first end of the first channel of the gap junction reactor;
    said second capillary being inserted through the second fitting and clamped by the second fitting in a second position in which its inlet end extends into a second end of said first channel such that said exit end of the first capillary and said inlet end of the second capillary are not overlapping, are aligned substantially collinearly and are separated by a gap; and
    a voltage source adapted to couple to fluid in said first and second capillaries to produce a voltage difference between the exit end of the first capillary and the inlet end of the second capillary.

15. A gap junction reactor as in claim 14 further comprising a heater attached to said body.

16. A gap junction reactor as in claim 14 wherein said first and second capillaries have different inside diameters.

17. A gap junction reactor as in claim 14 wherein said exit end of the first capillary and said inlet end of the second capillary are separated by a distance on the order of an inside diameter of one of the capillaries.

18. A gap junction reactor as in claim 14 further comprising:
    a lens attached to a side of said reactor such that a user can peer through this lens to optically magnify a section of said first channel.

19. A gap junction reactor as in claim 14 wherein said body is polymethyl pentene, whereby this body has a high degree of clarity and chemical inertness.

20. A gap junction reactor as in claim 14 further comprising:
- a source of an optical beam that is imaged onto said gap.

21. A gap junction reactor as in claim 20 further comprising:
a first optical fiber positioned and oriented in said gap reaction reactor to receive light travelling from said gap between the first and second capillaries.

22. A gap junction reactor as in claim 21 further comprising: a third fitting that positions and claims said first optical fiber to said gap junction reactor.

23. A gap junction reactor as in claim 22 further comprising:
a second optical fiber positioned and clamped to said reactor by a fourth fitting to direct said light beam through the gap.

24. A gap junction reactor as in claim 20 wherein said beam is directed through the gap without significantly overlapping onto said first and second capillaries, thereby reducing scatter off of said capillaries.

25. A gap junction reactor as in claim 24 further comprising:
a first optical fiber positioned and oriented in said gap reaction reactor to receive light travelling from said gap between the first and second capillaries.

26. A gap junction reactor as in claim 14 wherein said body also has a second channel that intersects the first channel, this first channel terminating at a third fitting adapted to receive a third capillary, whereby liquids can be inserted through this third capillary into the gap between the first and second capillaries.

27. A gap junction reactor as in claim 26 wherein the exit end of the first capillary and the inlet end of the second capillary each extends into an intersection of the first channel with the second channel.

* * * * *